(12) United States Patent
Thuot

(10) Patent No.: US 7,288,748 B1
(45) Date of Patent: Oct. 30, 2007

(54) PTC ELECTRICAL HEATING DEVICES

(75) Inventor: Raechell Maria Thuot, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 11/614,645

(22) Filed: Dec. 21, 2006

(51) Int. Cl.
*H05B 3/08* (2006.01)
*H01C 7/13* (2006.01)

(52) U.S. Cl. .................... 219/541; 219/540; 219/530; 219/517; 219/505; 338/22 R; 392/395; 392/391; 392/403; 392/485; 123/547; 361/104

(58) Field of Classification Search .............. 219/541, 219/540, 530, 517, 505, 504; 338/22 R; 392/395, 391, 403, 485, 480; 123/547; 361/104
See application file for complete search history.

(56) References Cited

U.S. PATENT DOCUMENTS

| 4,037,082 | A | 7/1977 | Tamada et al. |
| 4,251,714 | A | 2/1981 | Zobele |
| 4,635,026 | A | 1/1987 | Takeuchi |
| 4,728,779 | A | * | 3/1988 | Kotani et al. ............. 219/517 |
| 4,814,584 | A | 3/1989 | Bohlender et al. |
| 4,874,924 | A | 10/1989 | Yamamoto et al. |
| 5,262,619 | A | 11/1993 | Karner |
| 6,192,169 | B1 | 2/2001 | Cammons et al. |
| 6,374,045 | B2 | 4/2002 | Basaganas Millan |
| 7,012,225 | B2 | 3/2006 | Bohlender et al. |

FOREIGN PATENT DOCUMENTS

| EP | 0290159 B1 | 12/1994 |
| EP | 0591537 B1 | 11/1996 |
| EP | 965267 | 12/1999 |
| WO | WO 97/02054 | 1/1997 |
| WO | WO 97/45008 | 12/1997 |
| WO | WO 98/57674 | 12/1998 |
| WO | WO 2006/046209 | 5/2006 |

OTHER PUBLICATIONS

A Sep. 1, 2006 web site excerpt showing a Legobrick.

* cited by examiner

*Primary Examiner*—Shawntina Fuqua

(57) ABSTRACT

PTC electrical heating devices are disclosed which are suitable to vaporize air treatment chemicals from an impregnated slab, such as insect repellents. In one form an electrical contact to a PTC heater element is provided with a bowl-shaped contact head to reduce the risk of edges of the contact cracking the heater element. In other forms peg and recess structures interact with apertures on a heat transfer plate to facilitate assembly of the parts of the structure.

12 Claims, 4 Drawing Sheets

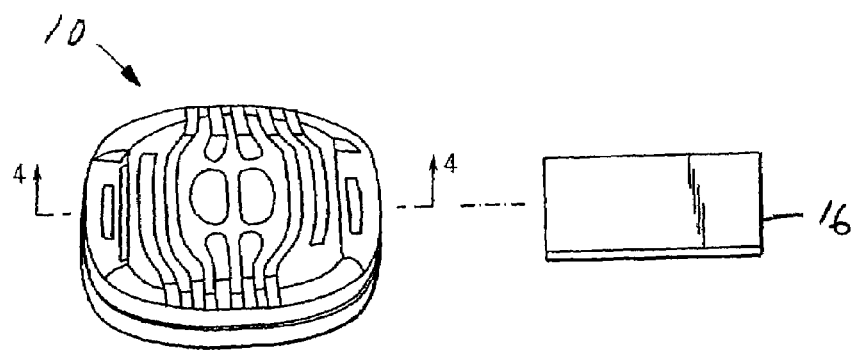
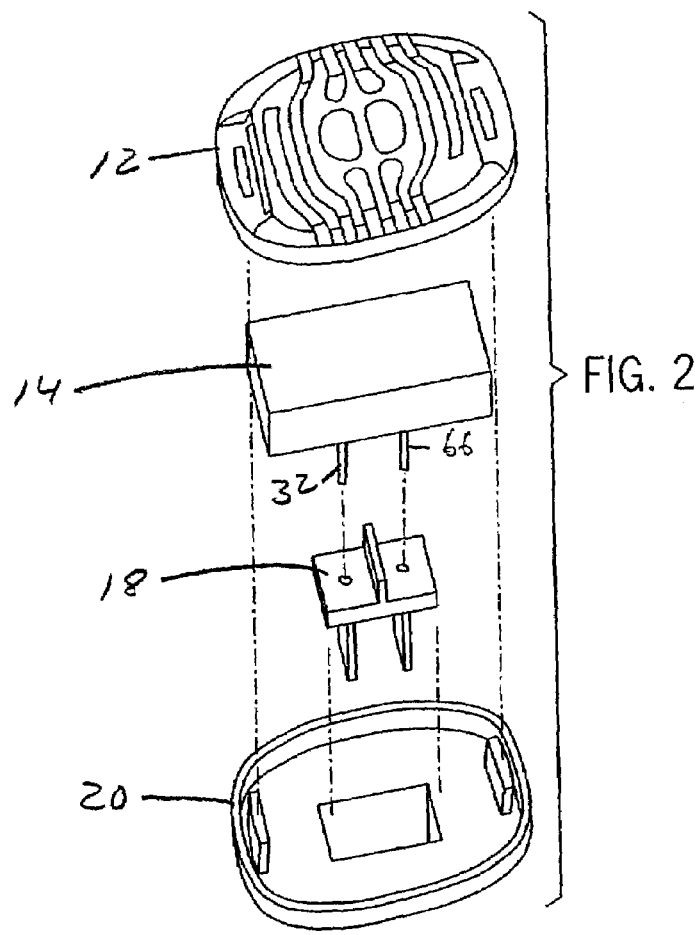

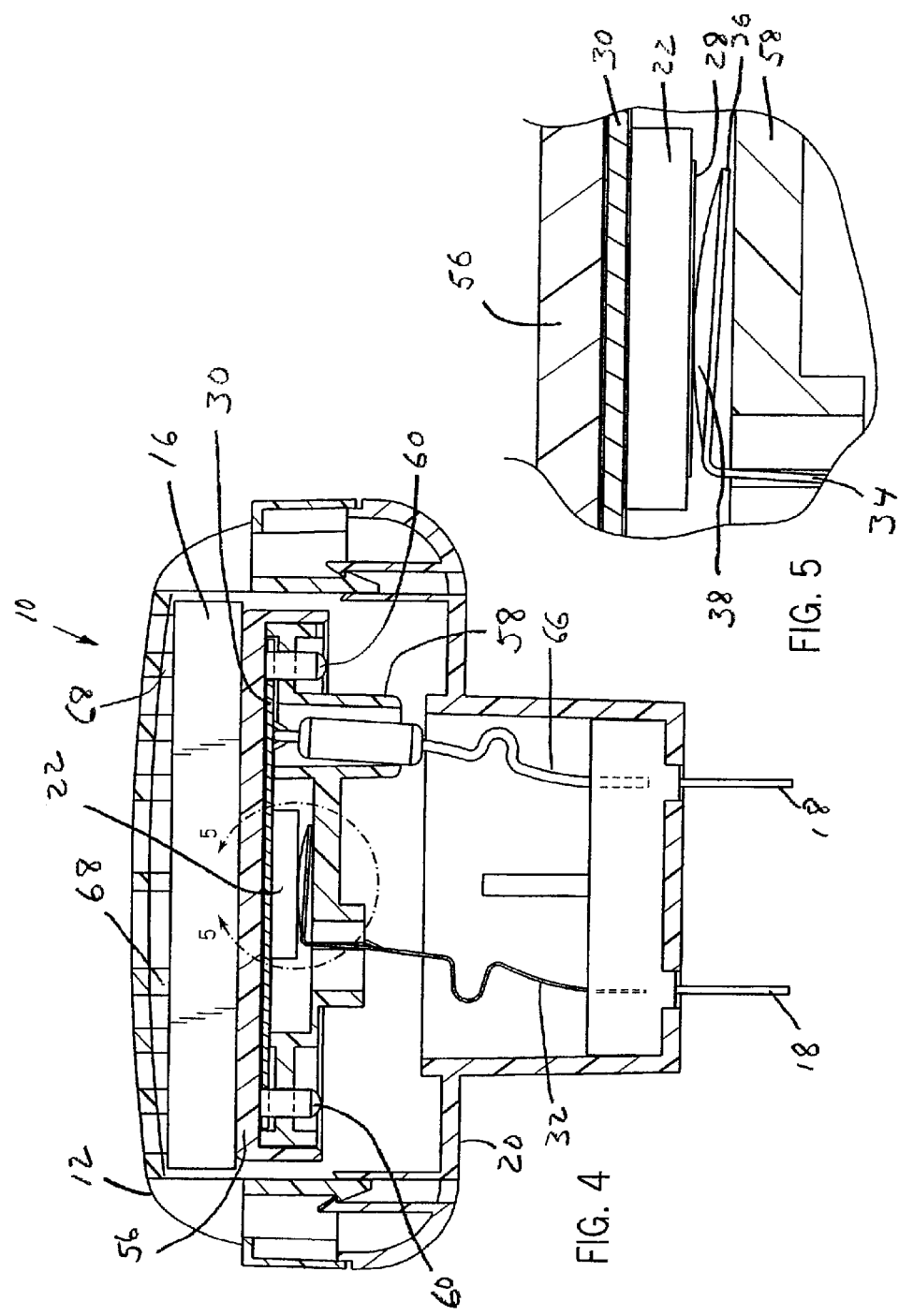

PTC ELECTRICAL HEATING DEVICES

CROSS-REFERENCE TO RELATED APPLICATIONS

Not applicable.

STATEMENT REGARDING FEDERALLY SPONSORED RESEARCH/DEVELOPMENT

Not applicable.

BACKGROUND OF THE INVENTION

The present invention relates to positive temperature coefficient ("PTC") heaters used to vaporize insect control agents (e.g. repellents, insecticides, growth regulators), fragrances, and other air treatment chemicals (e.g. deodorizers) from an impregnated substrate. More particularly it relates to improved electrical contacts and structural assemblies for such devices.

A variety of electrical heaters have been developed on which, or through which, substrates impregnated with air treatment chemicals are placed. Heating of the substrate by such devices causes the air treatment chemical, such as allethrin, or any of various other commercially known vaporizable insecticides, to vaporize. While such devices can be powered by battery, they are typically designed to be plugged into electrical outlets.

A particularly preferred form of such electrical heaters uses a PTC heating element. However, such devices can experience some maintenance issues associated with the fragile nature of preferred PTC heating element materials and the structure of associated electrical contacts. In this regard, many PTC elements are somewhat fragile and their abutment with associated electrical contacts (particularly those that are stamped) can on occasion lead to breakage of the PTC element due to interaction of that element with an edge of the contact.

WO 2006/046209 (the disclosure of which is hereby incorporated by reference as if fully set forth herein) discloses a particularly desirable form of PTC electric heating device for vaporizing insecticides and fragrances impregnated in a solid mat. While this form of heater has many advantages, it still has some drawbacks.

For one thing, the electrical terminal/contact which has a pressure contact with the PTC heating element is a stamped part. As a result, there will occasionally be sharp edges formed on the contact. When these edges come into contact with the fragile PTC heater element, there can be an incidence of cracking of the PTC heater element, either when the electric heater device is being manufactured, shipped or handled, or as it heats and cools through use.

A variety of heating elements have been developed for these and analogous applications. See generally U.S. Pat. Nos. 4,037,082, 4,251,714, 4,635,026, 4,728,779, 4,814,584, 5,262,619, 6,192,169, 6,374,045, 7,012,222, and international publications WO 97/02054, WO 97/45008, and WO 98/57674; and European patent application EP 965 267. However, these were each deficient in some attribute.

Hence, a need still exists for improved PTC electrical heating devices useful for vaporizing air treatment chemicals.

BRIEF SUMMARY OF THE INVENTION

In one aspect the invention provides a heating device suitable to vaporize an air treatment chemical. The air treatment chemical can be, by way of non-limiting example, impregnated into or on a wick, a conventional mosquito mat, or other substrate, with the heating device including an arrangement to mount the impregnated substrate where it can be heated when the heating device is activated. The device has a PTC heating element, and a first electrical contact abutting the PTC heating element. In accordance with the invention, the first electrical contact has a domed contact head, having a convexly curved surface presented toward the PTC heating element.

In preferred forms there is also a second electrical contact contacting the PTC heating element on a side thereof opposite a side to which the first electrical contact abuts, the first electrical contact also has a spring bend and a circular periphery, in plan view, with respect to the domed contact head, the domed contact head has a continuously curved outer edge, and the domed contact head has a convex side and a concave side, with the convex side being presented toward the PTC heating element.

The first electrical contact head may be formed of metal, a suitably resilient stainless steel being preferred, and may have a snap tab below its head. The snap tab can be so placed and sized as to secure the first electrical contact in a housing. Preferably, the domed contact head is capable of elastic deformation such that the domed contact head elastically deforms when pressed against the PTC heating element, reversibly increasing the area of contact of the domed contact head with the PTC heating element.

In another aspect the device may also have a first and second heater housings, and a second electrical contact in the form of a plate with an aperture. At least one of the heater housings has a peg and the other heater housing has a receiving recess. The peg passes through the plate aperture and into the receiving recess.

In a preferred embodiment, the device is designed to be used with an impregnated mat, such as a common mosquito mat formed of compressed cellulosic fibers and impregnated with an insect control agent such as allethrin that can volatize from the mat when the mat is heated. The art is well aware of a number of other insect control agents commonly used to dose mosquito mats intended for use with a heater device.

In another form the invention provides an electrical contact suitable for use with a PTC heating device. The contact has a domed head in the form of a bowl, and a leg extending below the head for linkage to a terminal. There can also be a snap tab located on the leg and a spring bend formed in the leg.

It should be appreciated that the use of such domed contact heads, particularly when the head is bowl form, keeps any edge of the head which might have burrs or other sharp remnants from formation, away from the fragile PTC heater. Hence, the risk of such defects causing PTC heater element cracks over time is eliminated.

Further, the combination of such a head with associated spring bends and snap tabs renders the contact suitable to optimize pressure against the PTC heater element while also positioning the contact relative to other assembly parts. Preferably, the domed contact head is capable of elastic deformation such that the domed contact head elastically deforms when pressed against the PTC heating element, reversibly increasing the area of contact of the domed contact head with the PTC heating element.

Also, the use of the peg and recess assembly technique reduces stress placed on the PTC heating element in the course of the assembly of the device, reducing the danger of cracking the PTC heating element.

The foregoing and other advantages of the present invention will become apparent from the following description. In that description reference is made to the accompanying drawings which form a part thereof, and in which there is shown by way of non-limiting illustration a preferred embodiment of the invention.

BRIEF DESCRIPTION OF THE DRAWINGS

FIG. 1 is a perspective view of an embodiment of the invention, shown with an impregnated mat about to be installed therein;

FIG. 2 is an exploded perspective view of the FIG. 1 embodiment, albeit without the impregnated mat shown;

FIG. 4 is a cross-sectional view taken along line 4-4 of FIG. 1;

FIG. 5 is a detail view of detail 5-5 of FIG. 4;

DETAILED DESCRIPTION OF THE PREFERRED EMBODIMENTS

Figure 3:
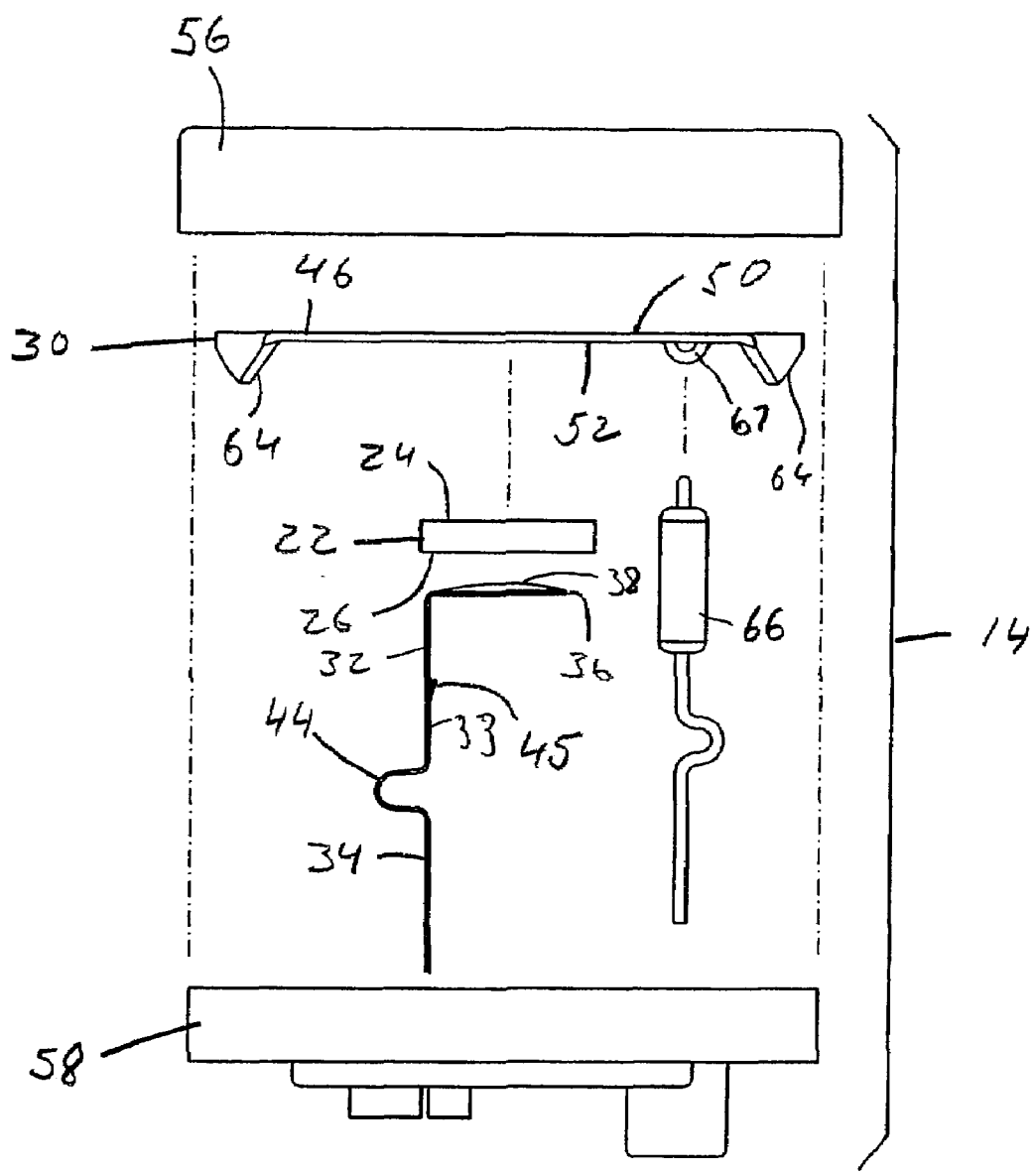
FIG. 3 is an exploded perspective view of a PTC heater of the FIG. 1 device.

Referring first to FIGS. 1 and 2, there is shown a vaporizer 10 which includes an apertured cover 12, a PTC heater 14, an impregnated mat 16, plug terminals 18, and a bottom housing 20. For convenience of description, the direction toward the cover 12 will be referred to as "up," even though in actual use the vaporizer may be used in any orientation. Terminals 18 can plug into a typical electrical outlet. It should be understood that while a two-prong plug configuration is suitable for certain countries, the terminals 18 will be modified as necessary to conform to plug standards used in other countries.

As will be apparent from FIG. 3, PTC heater 14 includes a PTC heating element 22 having a first side 24 and a second side 26 opposite first side 24. While PTC heating element 22 is shown in a round, "pill" form, other conventional PTC element shapes could also be used. In any event, as indicated in FIG. 5, PTC heating element 22 can have metallization 28 on side 26, and a similar metallization can be provided along first side 24 (not shown).

A heat transfer plate 30 contacts first side 24, and electrical contact 32 contacts second side 26 (through their respective metallization surfaces, if metallization is present). Contact 32 preferably includes an elongated leg 34, a spring bend 44, a connector segment 33 above the spring bend 44, and an upwardly curved dome 36 having a contact portion 38. Note that dome 36 exposes no edge surfaces to the PTC heating element 22. Hence, no remnants from stamping or other forming operations along the lower edge of the dome 36 can contribute to any breakage of the PTC heating element 22. In use, the contact portion 38 is pressed against side 26 of the PTC heating element 22, making firm contact. The dome 36 can be made of a resilient material, such as a sufficiently thin metal, such that it elastically deforms when pressed against the PTC heating element 22, reversibly flattening or even inverting a small area or the contact portion 38 (not shown). This increases the area of contact of the dome 36 with the PTC heating element 22, allowing for a more effective electrical contact and for a spring-like action that adjusts to changes in the size of the PTC heating element as it expands upon heating or contracts upon cooling.

Figure 7:
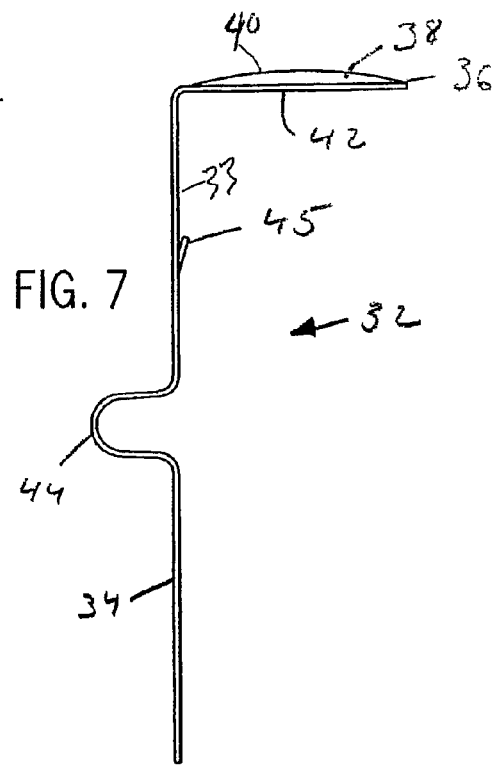
FIG. 7 is a side view of an electrical contact of the PTC heater.
Figure 8:
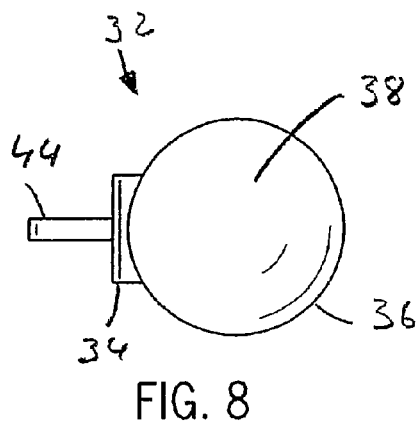
FIG. 8 is a top view of the electrical contact of FIG. 7.

As shown in FIG. 7, the dome 36 can have a convex side 40 and a concave side 42. While dome 36 is shown in one form, it should be appreciated that it could be more spherical, and in any event can have a non-constant plan view radius (e.g. elliptical or other curved contact surfaces). Note that there can also be a snap tab 45 to facilitate positioning as shown in FIG. 4.

Note that transfer plate 30 has a conductive plate 46 which contacts first side 24. This conductive plate 46 can comprise planar central portion 48 with sides 50 and 52. There is also a perimeter 54 and apertures 55.

Figure 6:
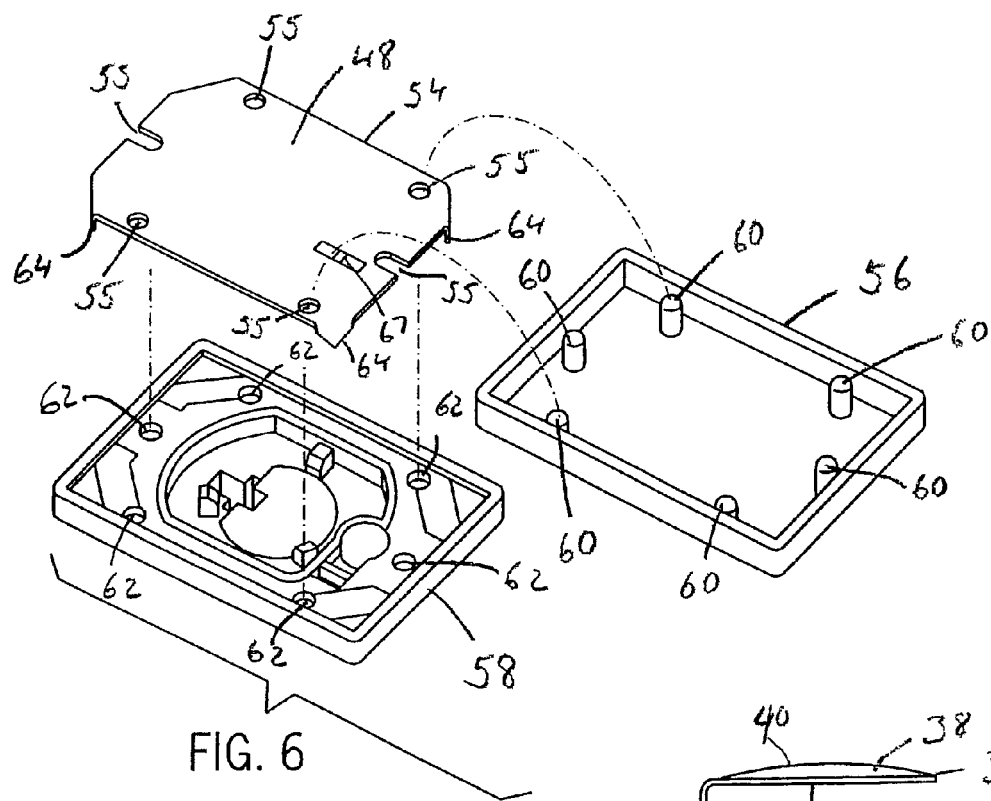
FIG. 6 is a partially exploded perspective view of the FIG. 3 PTC heater, albeit only showing certain parts.

As shown in FIGS. 3 and 6 there is also a first heater housing 56, and a second heater housing 58 forming a clamshell type housing. First heater housing 56 has pegs 60, and second heater housing 58 has receiving holes 62, such that the heater housing parts can be assembled by inserting the pegs into the holes, optionally followed by sonic or heat welding. Note that the pegs are designed to also fit through apertures 55 which also results in conductive plate 46 being fixed in place.

Bent corners 64 on heat transfer plate 30 help maintain a positive pressure contact between heat transfer plate 30 and first heater housing 56, which facilitates a relatively efficient heat transfer from PTC heating element 22 to first heater housing 56, and then to mat 16. Upon heating of the mat the air treatment chemical is dispensed. In this way heat transfer plate 30 acts not only as an electrical contact, it also spreads out and transfers heat generated by PTC heating element 22.

A fusible resistor 66 preferably is included in the electrical circuit by connecting to heat transfer plate 30 at contact 67. Should the heater 14 overheat, the fusible resistor 66 opens, halting the flow of electrical current through PTC heating element 22, thus providing protection for the overall device. The fusible resistor 66 and contact 32 via elongated leg 34 connect into plug terminals 18. As shown in FIG. 4, ribs 68 of cover 12 hold mat 16 against PTC heater 14 when the mat 16 is installed in vaporizer 10.

To use the device of the present invention, one plugs terminals 18 into an electrical outlet, thereby causing heat to be generated by PTC heating element 22, thereby heating the impregnated mat and causing air treatment chemicals to be dispensed thereby. The nature of the substrate used for the mat is not critical, nor is what impregnates it. For purposes of this invention, the key features relate to the domed structure of the contact.

While this invention has been described with reference to a particular embodiment, the present invention can be modified within the spirit and scope of this disclosure. For example, the form of the dome 36 of the contact need not be exactly as shown. Rather, the key portion of the concept is that no edge of the contact along the head be positioned where it can come into contact with the PTC resistance heater.

This application is therefore intended to cover variations, uses, or adaptations of the invention using its general principles. Thus, the claims should be looked to in order to judge the full scope of the invention.

INDUSTRIAL APPLICABILITY

The present invention provides a PTC type heater which can be produced inexpensively and has improved maintenance characteristics.

What is claimed is:

1. A heating device suitable to vaporize an air treatment chemical, the device comprising:
    a PTC heating element; and
    a first electrical contact abutting the PTC heating element;
    wherein the first electrical contact has a domed contact head having a convexly curved surface presented toward the PTC heating element;
    whereby the domed contact head contacts the PTC heating element without an edge of the head also contacting the PTC heating element.

2. The heating device of claim 1, further comprising a second electrical contact contacting the PTC heating element on a side thereof opposite a side to which the first electrical contact abuts.

3. The heating device of claim 1, wherein the domed contact head is capable of elastic deformation such that the domed contact head elastically deforms when pressed against the PTC heating element, reversibly increasing the area of contact of the domed contact head with the PTC heating element.

4. The heating device of claim 1, wherein the first electrical contact has a circular periphery, in plan view, with respect to the domed contact head.

5. The heating device of claim 1, wherein the domed contact head has a continuously curved outer edge.

6. The heating device of claim 1, wherein the domed contact head has a convex side and a concave side.

7. The heating device of claim 1, wherein the device further comprises an impregnated substrate, and wherein the substrate is impregnated with an insect control agent that can volatize from the substrate when the substrate is heated.

8. An electrical contact suitable to contact a PTC heating element of a PTC heating device, the electrical contact comprising:
    a domed head in a form of a bowl; and
    a leg extending below the head for linkage to a terminal;
    wherein the electrical contact has a continuously curved outer edge, in plan view, with respect to the domed contact head; and
    whereby the domed contact head is suitable to contact the PTC heating element without an edge of the head contacting the PTC heating element.

9. The electrical contact of claim 8, wherein the domed head is capable of elastic deformation such that the domed contact head elastically deforms when pressed against the PTC heating element, reversibly increasing the area of contact of the domed head with the PTC heating element.

10. The electrical contact of claim 8, wherein the electrical contact also has a spring bend.

11. The electrical contact of claim 8, wherein the electrical contact also has a snap tab.

12. The heating device of claim 1, further comprising:
    a first heater housing;
    a second heater housing; and
    a second electrical contact in a form of a plate with an aperture;
    wherein at least one of said heater housings has a peg and the other heater housing has a receiving recess, wherein the peg passes through the plate aperture and into the receiving recess.

* * * * *